United States Patent
Yokota et al.

(10) Patent No.: US 9,757,103 B2
(45) Date of Patent: Sep. 12, 2017

(54) METHOD FOR INSERTING ENDOSCOPIC DEVICE INTO HOLLOW ORGAN

(71) Applicant: OLYMPUS CORPORATION, Tokyo (JP)

(72) Inventors: Takuo Yokota, Hino (JP); Rei Matsunaga, Hino (JP); Kunihide Kaji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 398 days.

(21) Appl. No.: 14/526,967

(22) Filed: Oct. 29, 2014

(65) Prior Publication Data

US 2016/0121083 A1 May 5, 2016

(51) Int. Cl.
| A61B 1/00 | (2006.01) |
| A61B 17/00 | (2006.01) |
| A61M 25/09 | (2006.01) |
| A61F 2/966 | (2013.01) |
| A61B 1/04 | (2006.01) |

(Continued)

(52) U.S. Cl.
CPC ........ *A61B 17/00234* (2013.01); *A61F 2/966* (2013.01); *A61M 25/09041* (2013.01); *A61B 17/29* (2013.01); *A61B 17/3415* (2013.01); *A61B 17/3478* (2013.01);

(Continued)

(58) Field of Classification Search
CPC ............ A61M 25/09; A61M 25/09041; A61B 17/00234; A61B 17/29; A61B 2017/00296; A61B 2017/003; A61B 1/273; A61B 1/2733; A61B 1/2736
See application file for complete search history.

(56) References Cited

U.S. PATENT DOCUMENTS 6,461,296 B1 * 10/2002 Desai ................... A61B 8/0841
  600/210
2009/0054927 A1 * 2/2009 Agnew .............. A61B 17/0057
  606/213

(Continued)

FOREIGN PATENT DOCUMENTS

| JP | A-2008-289556 | 12/2008 |
| JP | A-2012-524616 | 10/2012 |
| WO | WO 2010/082399 A1 | 7/2010 |

OTHER PUBLICATIONS

Dhir et al., "EUS-guided biliary rendezvous using a short hydrophilic guidewire,"*J Interv Gastroenterol*, 2011, vol. 1, No. 4, pp. 153-159.

*Primary Examiner* — Timothy J Neal
(74) *Attorney, Agent, or Firm* — Oliff PLC

(57) ABSTRACT

In a method for inserting an endoscopic device, a guide wire is punctured into a subject from outside the body. A tip portion of the wire is inserted into a first hollow organ. A tip-side portion of the inserted wire is projected into a lumen of a second hollow organ that communicates with the first via an opening, from the opening. An endoscopic device is inserted through a flexible endoscope and pushed into the second hollow organ. A tip portion of the device is locked onto the tip-side portion of the wire projecting into the second hollow organ. A portion of the wire outside the body of the subject is held and is tugged outside of the body. The tip portion of the device is thus pulled into the first hollow organ from the second, via the opening. Therefore, the endoscopic device can be led to the first hollow organ.

20 Claims, 9 Drawing Sheets

(51) Int. Cl.
A61B 17/29 (2006.01)
A61B 17/34 (2006.01)
A61F 2/04 (2013.01)

(52) U.S. Cl.
CPC ............ *A61B 2017/0034* (2013.01); *A61B 2017/00818* (2013.01); *A61F 2002/041* (2013.01)

(56) References Cited

U.S. PATENT DOCUMENTS

2010/0042077 A1  2/2010  Okada
2010/0179383 A1  7/2010  Motai et al.
2010/0268029 A1  10/2010  Phan et al.

* cited by examiner

METHOD FOR INSERTING ENDOSCOPIC DEVICE INTO HOLLOW ORGAN

BACKGROUND OF THE INVENTION (Field of the Invention)

The present invention relates to a method for inserting an therapeutic device into a hollow organ of a subject (such as a patient). In particular, the present invention relates to an insertion method that is suitable for cases in which, for example, an therapeutic device is inserted into a hollow organ, such as the bile duct or the pancreatic duct, through an opening, such as the duodenal papilla.

(Description of the Related Art)

For diseases involving a hollow organ of the human body, an therapeutic device may be inserted into the hollow organ using a guide wire. However, when an obstruction is present in the opening that leads to the hollow organ, the guide wire itself may not be able to be inserted into the hollow organ. For example, the duodenal papilla may be firmly closed. Alternatively, the orientation of the opening may significantly differ from the advancing direction of the therapeutic device. In such instances, insertion of the guide wire into the target lumen, such as the bile duct or the pancreatic duct, via the duodenal papilla may become difficult.

In such instances, a procedure referred to as a rendezvous method may be performed. In the rendezvous method, the bile duct is punctured from the gastrointestinal tract, such as the stomach. The guide wire is then antegradely indwelt. In this method, the guide wire, which projects into the duodenum from the duodenal papilla, is pulled outside of the body via a channel of an endoscope that has been inserted into the duodenum. Stent indwelling and the like are performed using the guide wire that has been pulled outside of the body.

To indwell an endoscopic device, such as a stent, using this procedure, in a manner similar to ordinary endoscopic retrograde cholangiopancreatography (ERCP), the endoscopic device is pushed into the papilla via an endoscope channel. As a result of the endoscopic device being pushed in this way, the endoscopic device can be indwelt in the bile duct or the pancreatic duct. However, for some reason involving the anatomical structure of the patient, the papilla may not be visible from the front in an endoscopic image or the papilla may be tightly closed. In addition, the running (anatomy) of the bile duct imagined by an operator may differ from the actual running (anatomy). In such instances, even when the operator attempts to push the endoscopic device into the papilla by manual operation, the endoscopic device may bend in the space between the tip of the endoscope and the papilla, causing loss of force. Insertion of the endoscopic device then becomes difficult.

SUMMARY

Therefore, it is desired that a method be provided that enables an endoscopic device to be easily inserted into a bile duct or a pancreatic duct, even in cases where insertion of the endoscopic device into the bile duct or the pancreatic duct by pushing inwards is difficult.

In a typical example, there is provided a method for inserting a endoscopic device into a hollow organ, including: a first step of inserting a guide wire into a subject from outside of a body of the subject and inserting a tip end portion of the guide wire into a first hollow organ of the subject; a second step of projecting, into a lumen of a second hollow organ, from an opening, the guide wire that is inserted into the first hollow organ and indwelling a tip-side portion of the guide wire in the lumen, the second hollow organ communicating the first hollow organ via the opening; a third step of inserting an endoscopic device through a channel of a flexible endoscope that is inserted into the second hollow organ and pushing the endoscopic device into the second hollow organ; a fourth step of making a tip portion of the endoscopic device engage with a part of the tip-side portion of the guide wire that is projected into the second hollow organ; and a fifth step of tugging the guide wire outside of the body by holding a portion of the guide wire that is outside of the body of the subject, thereby bring the tip portion of the endoscopic device in the first hollow organ from the second hollow organ via the opening.

DETAILED DESCRIPTION OF THE PREFERRED EMBODIMENTS

An embodiment of a method for inserting an endoscopic device into a hollow organ within a subject of the present invention will be described with reference to the drawings.

To perform this insertion method, a flexible endoscope, and/or an ultrasound endoscope or a transabdominal ultrasound diagnostic apparatus that enables contact with an ultrasound probe from outside of the body are used. In addition, a guide wire and an endoscopic device, such as a catheter, that is inserted into a channel of the flexible endoscope are used. These constituent elements are all well known. An indwelling object, such as a stent, is provided in a detachable manner in the tip portion of the endoscopic device.

Figure 1:
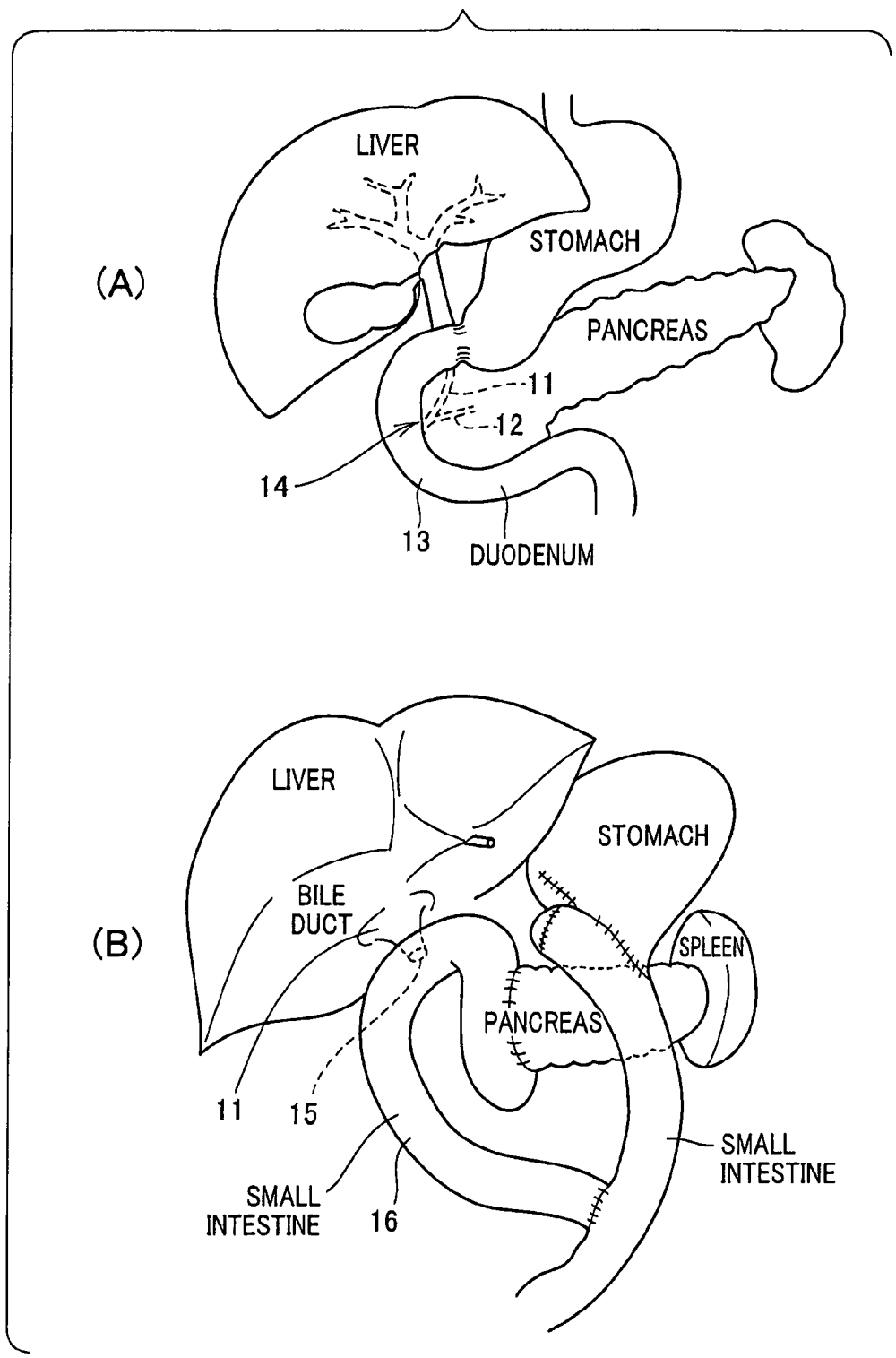
FIG. 1 is a diagram of anatomical examples in which a method for inserting an endoscopic device of the present invention can be performed, in which FIG. 1(A) and (B) explain two typical examples.

FIG. 1(A) and (B) show anatomical examples to which the insertion method of the present example can be applied.

FIG. 1(A) shows an anatomical example in which the papilla is not excised. In FIG. 1(A), a first hollow organ is the bile duct 11 or the pancreatic duct 12. The opening is the duodenal papilla 14. A second hollow organ is the duodenum 13 (see FIG. 1(B) for details). In addition, in FIG. 1(B), an anatomical example after a pancreaticoduodenectomy is shown. In this example, the papilla is excised. The bile duct/pancreatic duct are connected by anastomosis with the small intestine. The opening is an anastomotic site 15. The second hollow organ is the small intestine 16. The insertion method of the present example is favorably applied to an endoscopic ultrasound (EUS) rendezvous method performed for difficult ERCP cases such as this (refer to Vinay Dhir et al., "EUS-guided biliary rendezvous using a short hydrophilic guide wire", J Interv Gastroenterol 1:4, 153-159; October/November/December 2011; ©2011 Landes Bioscience).

Figure 2:
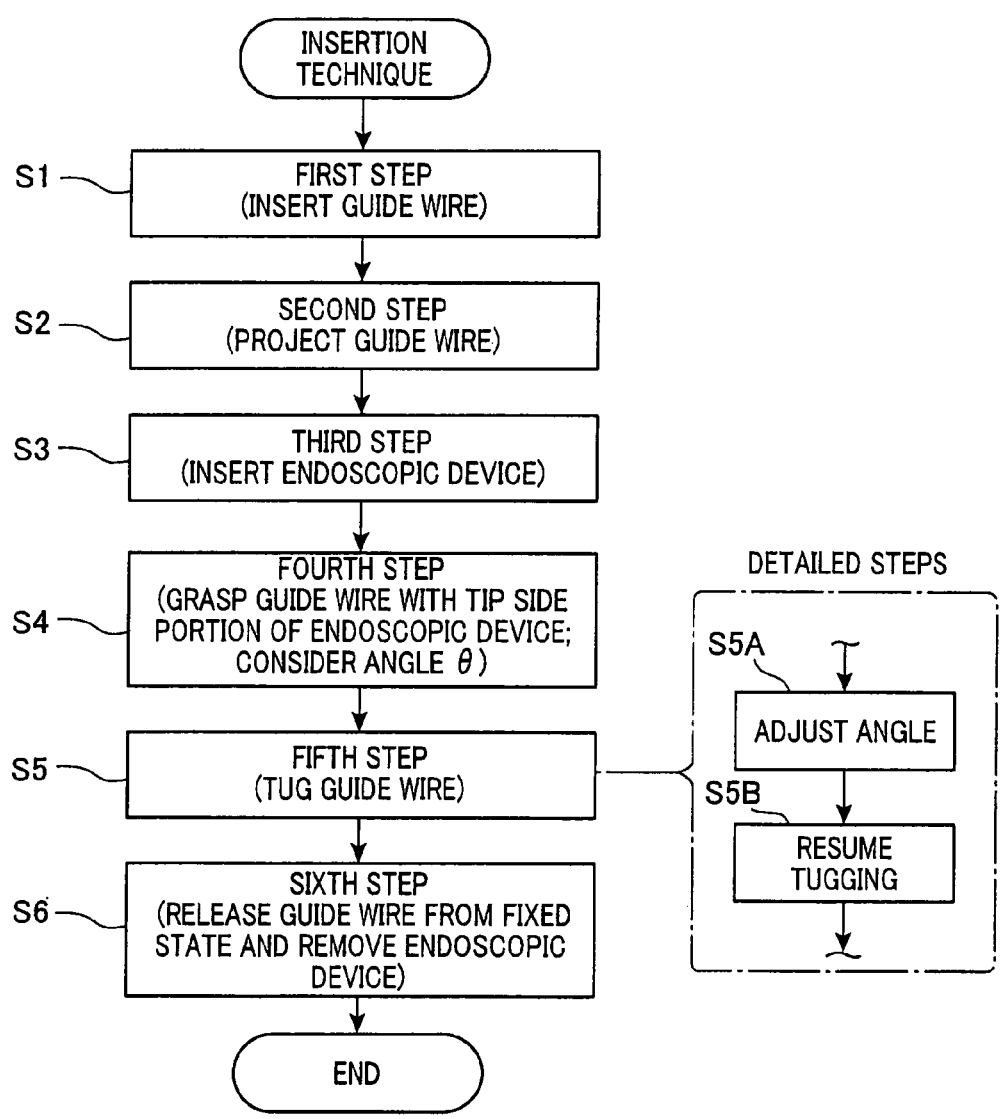
FIG. 2 is a flowchart for explaining the steps in the method for inserting an endoscopic device according to the present embodiment.

In FIG. 2, the insertion method (technique) according to the present embodiment that is manually performed by an operator (such as a doctor) is described so as to be organized into first to sixth steps. The following description references a drawing in which the papilla is not excised, such as that shown in FIG. 1(A). However, the method can also be applied to difficult ERCP cases as in FIG. 1(B). Therefore, the term "anastomotic site" is inserted and used as appropriate.

[First Step]

First, at a first step S1, the operator indwells a guide wire 21 in the bile duct 11 or the pancreatic duct 12. To puncture the bile duct 11 or the pancreatic duct 12, a method for puncturing from inside the body or a method for puncturing from outside of the body can be used.

When puncturing from inside the body, the ultrasound endoscope is used. First, the ultrasound endoscope is orally inserted into the gastrointestinal tract. Next, the bile duct or the pancreatic duct is confirmed through an ultrasound image. The target lumen is then punctured by a puncturing needle. When the site to be punctured is the bile duct, the intrahepatic bile duct may be punctured from the esophagus or the stomach (see FIG. 3(A)). Alternatively, the extrahepatic bile duct may be punctured from the duodenum. When the site to be punctured is the pancreatic duct, the pancreatic duct is punctured from the stomach or the duodenum. The guide wire 21 is inserted into the puncturing needle. The tip of the guide wire 21 is then inserted into the target lumen (the bile duct or the pancreatic duct).

When puncturing from outside of the body, a transabdominal ultrasound apparatus is used. The intrahepatic bile duct is confirmed from outside of the body using an ultrasound image. The bile duct is then punctured by a puncturing needle. Thereafter, the guide wire 21 is indwelt in a manner similar to that when puncturing is performed from inside the body.

[Second Step]

Figure 3:
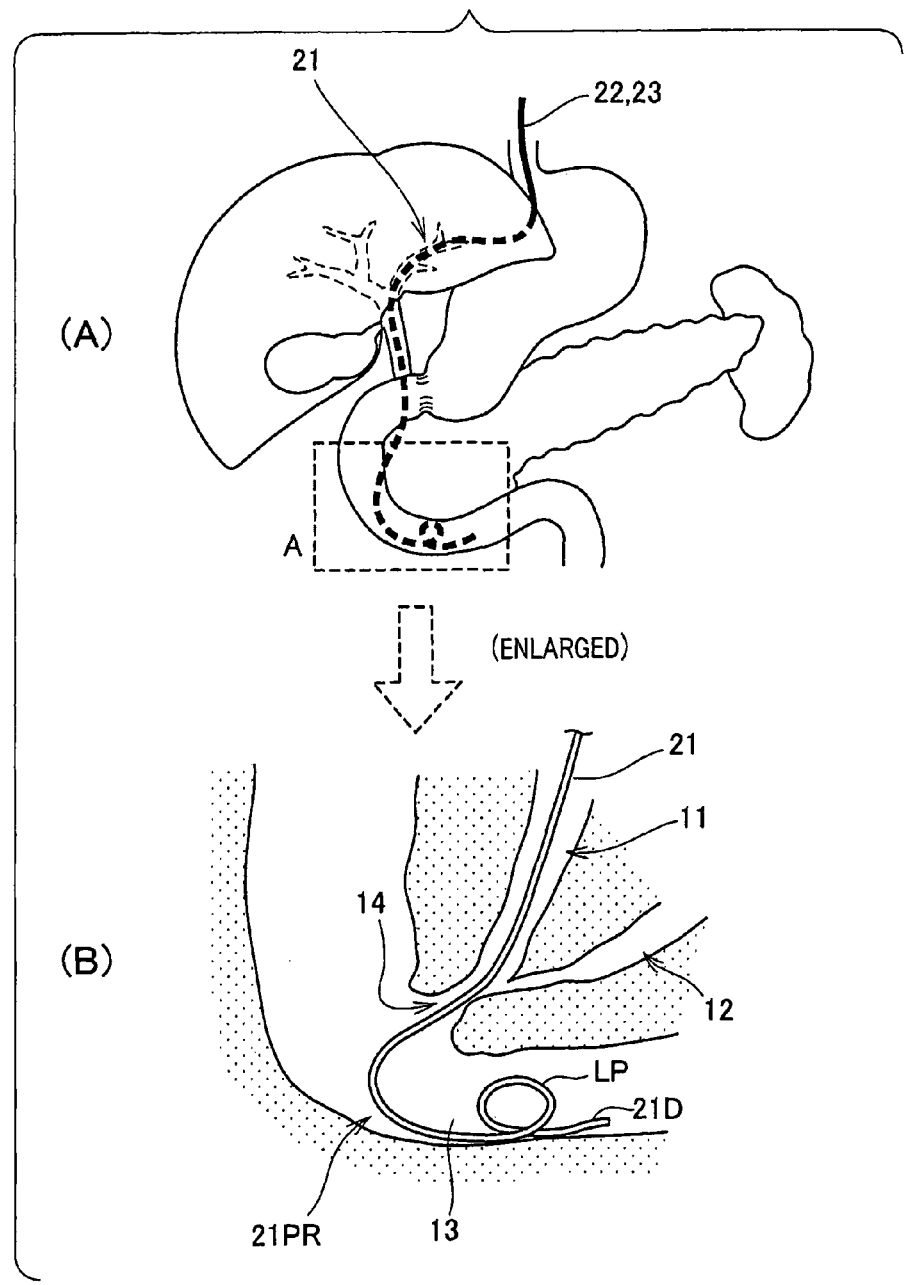
FIG. 3 is a schematic diagram for explaining a step in the insertion method, in which FIG. 3(B) explains section A in FIG. 3(A) using an enlarged view.

As a second step S2, the operator further pushes forward the guide wire 21 that is inserted into the target lumen (such as the bile duct 11 shown in FIG. 3(A) and (B)). The operator projects a tip-side portion 21PR of the guide wire 21 through the duodenal papilla 14, towards the lumen of the duodenum 13. The tip-side portion 21PR has a desired length. At this time, as a result of the guide wire 21 being pushed forward, a part of the tip-side portion 21PR of the guide wire 21 ordinarily forms a loop LP in the lumen of the duodenum 13. As described hereafter, as a result of this loop LP, the guide wire 21 does not easily become dislocated from the duodenum 13 when the flexible endoscope, described hereafter, is removed outside of the body. In this way, the tip end portion 21PR of the guide wire 21, which has a desired length, can be indwelt in the lumen of the duodenum 13.

When puncturing is performed from outside of the body, the ultrasound endoscope and the puncture needle are removed outside of the body, leaving only the guide wire 21.

[Third Step]

Figure 4:
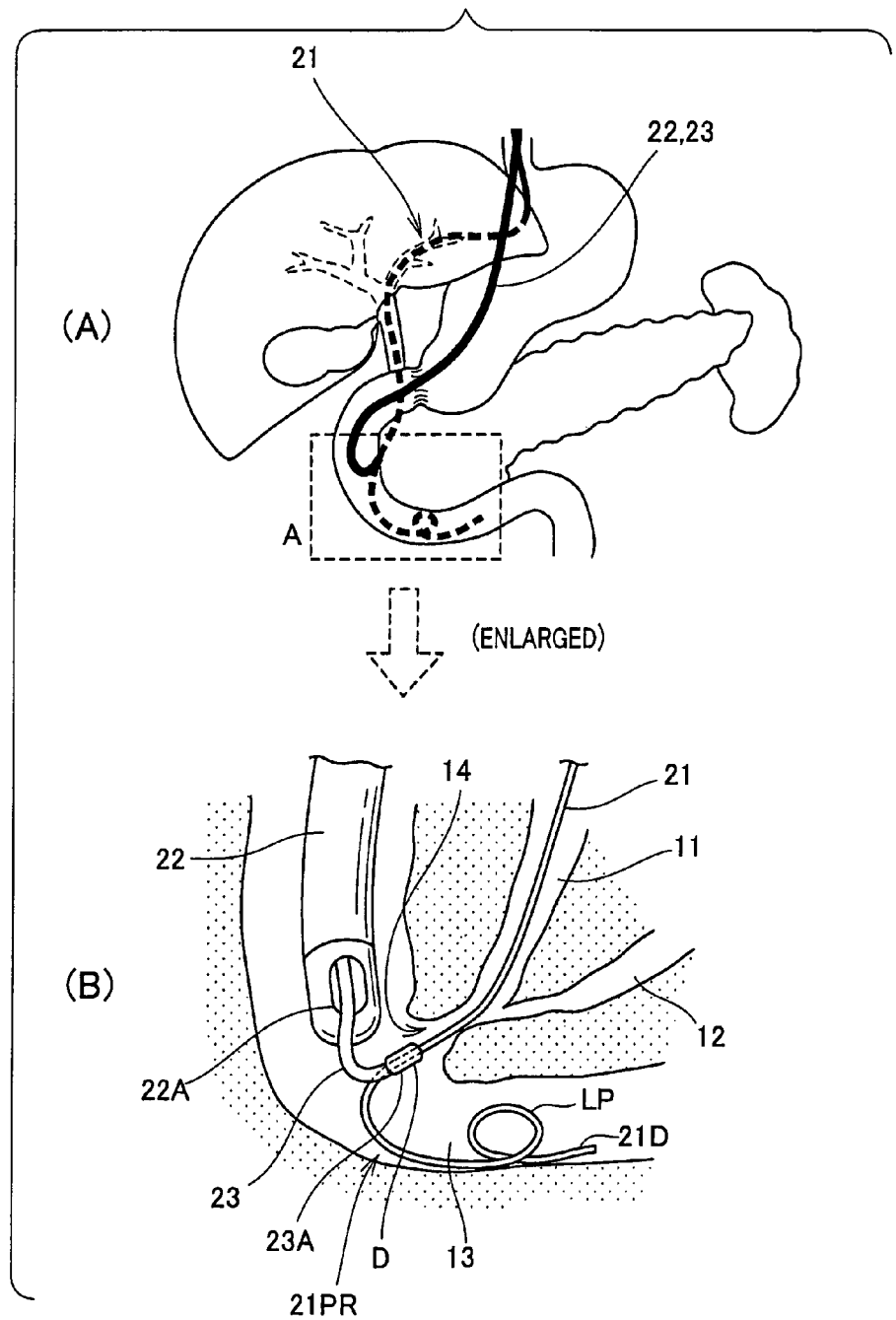
FIG. 4 is a schematic diagram for explaining another step in the insertion method, in which FIG. 4(B) explains section A in FIG. 4(A) using an enlarged view.
Figure 5:
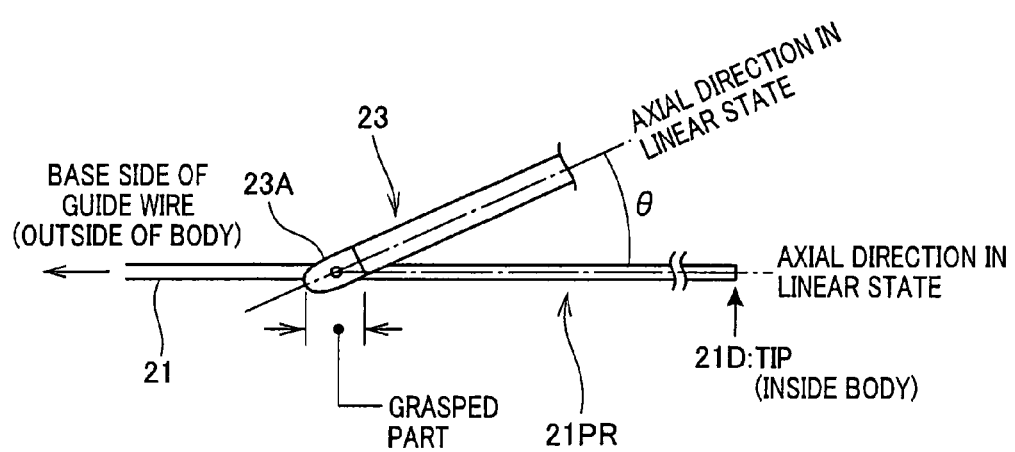
FIG. 5 is a diagram for explaining an engagement position of a grasping portion of the endoscopic device to a guide wire, and an angle formed between both axial directions of the grasping portion and the guide wire.

Next, as a third step S3, the operator orally inserts a flexible endoscope 22 for the duodenum to the vicinity of the papilla 14 of the duodenum (or the anastomotic site). FIG. 4 and FIG. 5 show an example of the papilla 14. An endoscopic device 23, such as grasping forceps, is inserted through a channel 22A of the flexible endoscope 22.

[Fourth Step]

Next, at a fourth step S4, while confirming the tip-side portion 21PR of the guide wire 21 that is projecting from the papilla 14 of the duodenum 13 in an endoscopic image, the operator makes the grasping portion 23A of the endoscopic device (such as the grasping forceps) 23 grasp a part of the tip-side portion 21PR of the guide wire 21 (see FIGS. 4(A) and (B)). The tip portion 21D of the guide wire 21 is thin and easily broken. Therefore, the part that is grasped by the grasping portion 23A is preferably a part midway between the vicinity of the tip portion 21D and the papilla 14, in the tip-side portion 21PR of the guide wire 21. Furthermore, when the loop LP is formed, the part that is grasped may be a part midway between the loop LP and the papilla 14, in the tip end portion 21PR of the guide wire 21.

[Fifth Step]

Figure 6:
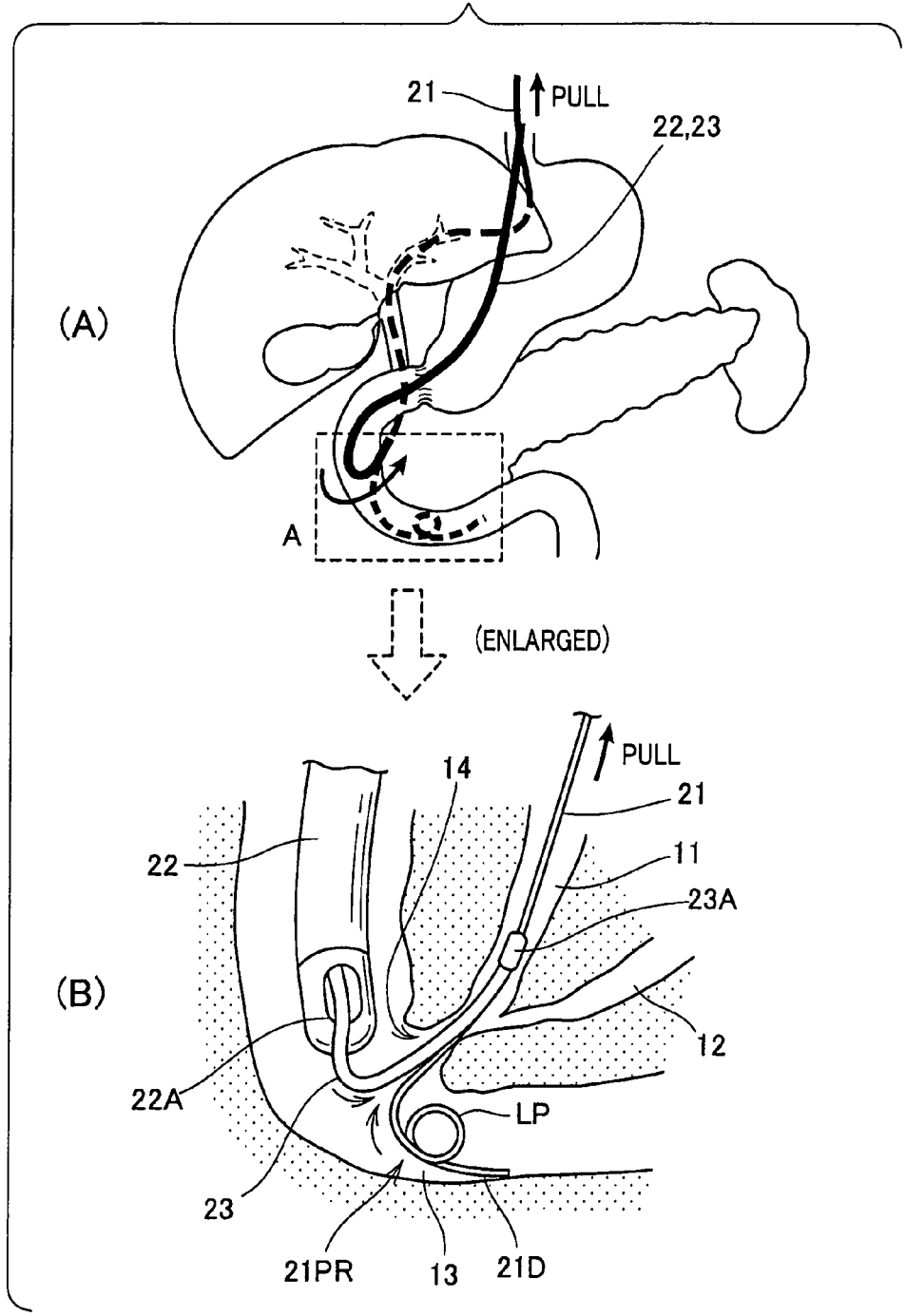
FIG. 6 is a schematic diagram for explaining a step in the insertion method, in which FIG. 6(B) explains section A in FIG. 6(A) using an enlarged view.

Next, as a fifth step S5, the operator manually pulls outward (in other words, towards the base side) one end of the guide wire 21 that is outside of the body of the subject or a portion in the vicinity thereof (in other words, a portion on the base side) outward (in other words, towards the base side) (see FIGS. 6(A) and (B)). As a result of this operation, the guide wire 21 that is projecting into the duodenum 13 is pulled into the papilla 14. In accompaniment with the pulling movement of the guide wire 21, the endoscopic device (grasping forceps) 23 that is grasping the guide wire 21 is also pulled into the papilla 14. Based on the subsequent pulling of the guide wire 21, the tip of the endoscopic device 23, or in other words, the grasping portion 23A advances upstream within, for example, the bile duct 11, as shown in FIG. 6(B).

During the tugging, the grasping portion 23A grasps the guide wire 21 so that an angle formed by the length directions of both the guide wire 21 and the endoscopic device 23 is as small as possible. In addition, the guide wire 21 is grasped so as to project from the tip of the grasping portion 23. Therefore, when the guide wire 21 is pulled, both the grasping portion 23A and the guide wire 21 move in the pulling direction. As a result, the grasping portion 23A does not interfere with the pulling, such as by the grasping portion 23A, or in other words, the tip portion of the endoscopic device 23 getting caught at the opening of the papilla 14. The pulling is smoothly performed.

In this way, even when the papilla (or the anastomotic site) is tightly closed, the endoscopic device 23, such as the grasping forceps, can be easily inserted into the papilla 14 (or the anastomotic site) as a result of the guide wire 21 being pulled. In addition, even when the opening direction of the papilla 14 (or the anastomotic site) differs from the advancing and retracting direction of the endoscopic device 23, the endoscopic device 23 can be easily inserted into the papilla 14 (or the anastomotic site).

To facilitate insertion of the endoscopic device 23 into the papilla 14 of the duodenum 13, the angle θ formed by the length directions of both the guide wire 21 and the endoscopic device 23 (grasping portion 23A) in a linear state is preferably as smaller than 90 degrees as possible (preferably as parallel as possible). In addition, the guide wire 21 is preferably grasped by the tip of the grasping portion 23A so that the guide wire 21 extends from the tip of the grasping portion 23A (see FIG. 5). This arrangement is merely required to be actualized immediately before the endoscopic device 23 is pulled into the papilla. Therefore, the endoscopic device 23 is merely required to grasp the guide wire 21 so as to achieve the arrangement shown in FIG. 5 at either the fourth step or the fifth step.

Specifically, to actualize the grasping state at Step S4, the operator can adjust the angle of the grasping portion 23A in the axial direction by manually manipulating the direction of the tip portion of the endoscope 22 or the like, under endoscope. In addition, to actualize the grasping state at Step S5, when the grasping portion 23A of the endoscopic device 23 advances to the papilla 14 (or the anastomotic site) and the angle θ at this time is a value near 90 degrees, for example, the operator can adjust the angle θ so as to be shifted to as small a value as possible, such as 20 degrees. In other words, because the grasping portion 23A is grasping with some play, the grasping state can be actualized by the operator manually adjusting the direction of the tip portion of the endoscope 22 or the like.

An example of the latter will be described. When the angle θ is large, and it is determined that the grasping portion 23A will have difficulty smoothly entering the papilla 14 (anastomotic site), the operator manually manipulates the direction of the tip portion of the endoscope 22 or the like, and adjusts the angle θ to a smaller value (Step S5A). As a result, the angle θ become smaller due to the play in the grasping state of the grasping portion 23A. When the adjustment is completed, tugging of the guide wire 21 is resumed (Step S5B). Even when the direction of the tip portion of the endoscope 22 or the like is not manually manipulated, for example, when the grasping portion 23A of the endoscopic device 23 is inserted into the opening of the papilla 14, adjustment may be made so that the angle θ is passively reduced as a result of the grasping portion 23A having some play.

In this way, the angle θ can be set to a value that is as smaller than 90 degrees as possible at either Step S4 or Step S5. Therefore, the endoscopic device 23 can be easily advanced into the papilla 14 of the duodenum 13 in accompaniment with the tugging of the guide wire 21.

In addition, when an indwelling object 31, such as a stent, is mounted in a detachable manner on the endoscopic device 23 in advance, the indwelling object 31 is also pulled into the papilla 14 (or the anastomotic site), together with the endoscopic device 23. The indwelling object 31 and the endoscopic device 23 can be easily inserted (see FIG. 7(A)).

[Sixth Step]

Figure 7:
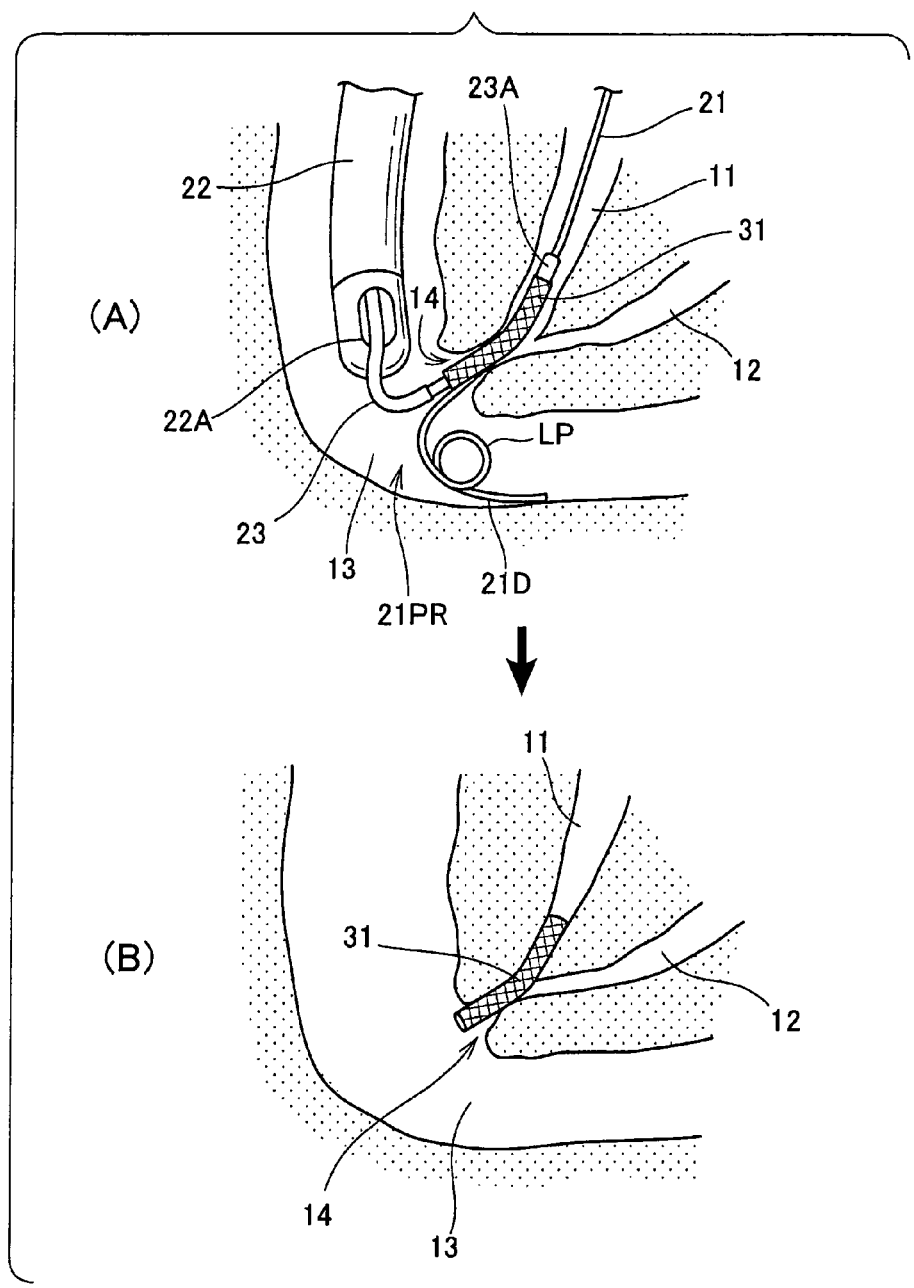
FIG. 7 is a schematic diagram for explaining indwelling of an indwelling object at an opening (papilla), in which FIG. 7(A) explains the movement of the indwelling object that moves together with the endoscopic device in accompaniment with tugging of the guide wire and FIG. 7(B) explains the indwelt state of the indwelling object.

Next, as a sixth step S6, after the indwelling (procedure) of the indwelling object 31, described above, is completed, fixing of the guide wire 21 by the endoscopic device 23 is released. The endoscopic device 23 is removed outside of the body. As a result, as shown in FIG. 7(B), the indwelling object 31 is indwelt in the papilla 14 (or the anastomotic site).

As described above, according to the present embodiment, a step of bringing in (or pulling) the guide wire 21, which is projecting into the duodenum 13, into an endoscope channel becomes unnecessary.

The operator inserts the endoscopic device 23 while pushing the endoscopic device 23 into the channel 22A of the endoscope 22 to lead the endoscopic device 23 to the duodenum 13. Subsequently, the operator engages the endoscopic device 23 to the guide wire 21 that projects into the duodenum 13. The guide wire 21 is then pulled from outside of the body. As a result of this pulling, the endoscopic device 23 is brought in the papilla 14. Compared to force required for pushing the endoscopic device 23, the indwelling object 31, or the like, the force required for bringing in the endoscopic device 23, the indwelling object 31, or the like is more easily transmitted to the endoscopic device 23, the indwelling object 31, or the like. Therefore, the endoscopic device 23, the indwelling object 31, or the like can be more easily inserted into the papilla 14.

VARIATION EXAMPLE

Figure 8:
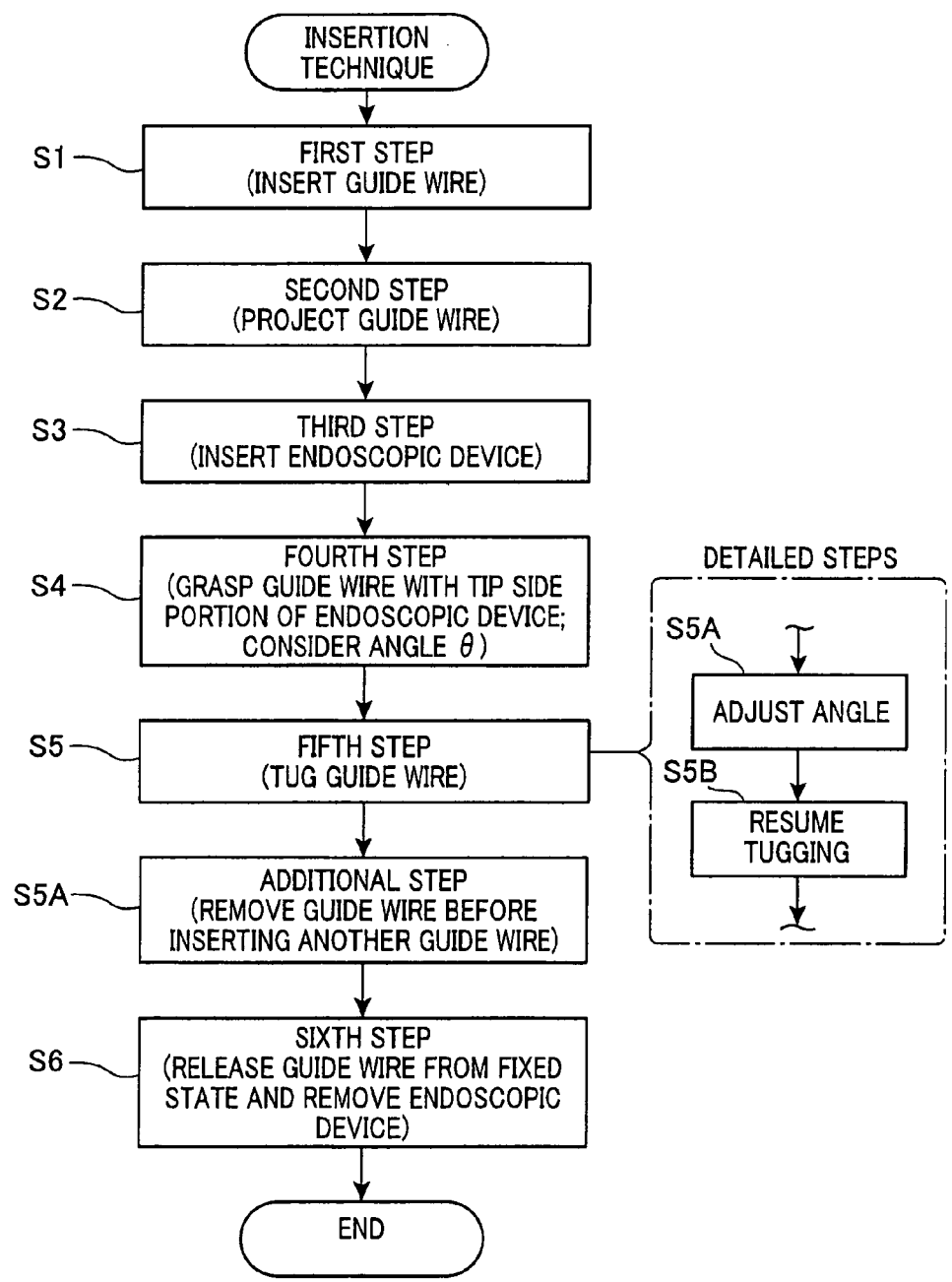
FIG. 8 is a flowchart for explaining the steps in the method for inserting an endoscopic device in a variation example of the example.

FIG. 8 shows a technique of a variation example. The basic content of the techniques at Step S1 to Step S6 is the same as that described above. In the present variation example, Step S5A is added after Step S5. At Step S5A, another (second) guide wire is passed through the grasping forceps inserted into the target lumen. The guide wire is endoscopically indwelt. At this time, the second guide wire is preferably indwelt in a state in which the first guide wire is grasped so that the grasping forceps do not become dislocated from the bile duct. When the second guide wire is indwelt, fixing of the first guide wire by the grasping forceps is released. The endoscopic device 23 and the first guide wire 21 are removed outside of the body, leaving the second guide wire (Step S6). As a result, the guide wire is endoscopically indwelt in the bile duct. Therefore, an ordinary ERCP procedure can be performed using the second guide wire.

Figure 9:
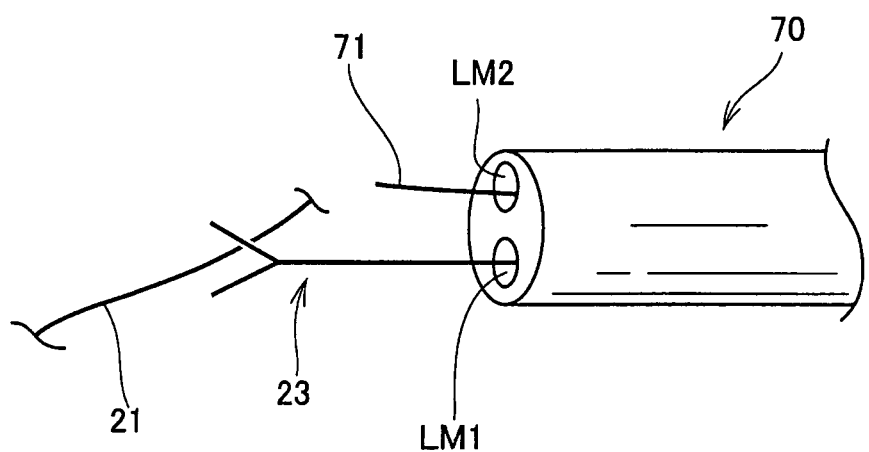
FIG. 9 is a diagram for explaining a more specific example of the variation example in FIG. 8.

More specifically, as shown in FIG. 9, the endoscopic device 23 may be used together with a guide sheath that has a plurality of lumens. FIG. 9 shows the tip portion of a guide sheath 70. The guide sheath 70 is positioned near the papilla 14, which serves as the opening, via the channel 22A of the endoscope 22. The endoscopic device 23 is used by being inserted into, for example, a first lumen LM1 of a plurality of lumens LM1 and LM2. When the guide sheath 70 is used, the tip portion of the guide sheath 70 is inserted into the papilla 14 with the tugging of the guide wire 21 (in other words, the insertion of the endoscopic device 23), in the process at Step S5. In this instance, after Step S5 or after the guide wire is released from the fixed state at Step S6, another guide wire 71 is inserted into the other second lumen LM2 of the plurality of lumens LM1 and LM2. The other guide wire 71 serves as an indwelling object. The tip portion of the guide wire 71 can be indwelt in the first hollow organ (such as the bile duct). Alternatively, a contrast agent can be injected into the bile duct or the like through the second lumen.

In this way, as a result of the method for inserting an endoscopic device in the present variation example being performed so as to be incorporated with the above-described embodiment, diversification of treatment can be addressed, in addition to facilitating the insertion of the endoscopic device.

The method for inserting an endoscopic device of the present invention is not necessarily limited to that described according to the above-described embodiment and variation example. Various aspects are further possible without departing from the scope of the present invention recited in the scope of claims.

What is claimed is:

1. A method for inserting an endoscopic device into a hollow organ, the method comprising:

a first step of inserting a guide wire into a subject from outside of a body of the subject and inserting a distal end portion of the guide wire into a first hollow organ of the subject;

a second step of projecting, into a lumen of a second hollow organ, from an opening, the guide wire that is inserted into the first hollow organ, and indwelling a distal-side portion of the guide wire in the lumen, the second hollow organ communicating with the first hollow organ via the opening;

a third step of inserting an endoscopic device through a channel of a flexible endoscope that is inserted into the second hollow organ, and pushing the endoscopic device into the second hollow organ;

a fourth step of engaging a distal end portion of the endoscopic device with a part of the distal-side portion of the guide wire that is projected into the second hollow organ; and a fifth step of pulling the guide wire from the body such that the wire is pulled outside of the body by holding a portion of the guide wire that is outside of the body of the subject, thereby bringing the distal end portion of the endoscopic device in the first hollow organ from the second hollow organ via the opening, wherein the first hollow organ is either a bile duct or a pancreatic duct, the opening is a duodenal papilla, and the second hollow organ is a duodenum.

2. The method of claim 1, wherein:
in the first step an ultrasound image is acquired by an ultrasound endoscope inserted into the second hollow organ through a natural opening of the subject; and
the guide wire is inserted into the first hollow organ while the ultrasound image is observed.

3. The method of claim 2, wherein:
in the third step the endoscopic device is pushed into the second hollow organ in a state where the endoscopic device has been inserted in the channel of the flexible endoscope and an indwelling object has been loaded on the distal end portion of the endoscope device; and
in the fifth step the guide wire is pulled from the body such that the wire is pulled outside of the body of the subject so as to bring the distal end portion of the endoscopic device in the first hollow organ from the second hollow organ via the opening together with the indwelling object.

4. The method of claim 1, wherein:
in the first step an ultrasound image is acquired by an ultrasound diagnostic apparatus that diagnoses the subject from outside of the body; and
the guide wire is inserted into the first hollow organ while the ultrasonic image is observed.

5. The method of claim 1, wherein:
in the third step the endoscopic device is pushed into the second hollow organ through the channel of the flexible endoscope in a state where an indwelling object has been loaded on the distal end portion of the endoscope device; and
in the fifth step the guide wire is pulled from the body such that the wire is pulled outside of the body of the subject so as to bring the distal end portion of the endoscopic device in the first hollow organ from the second hollow organ via the opening together with the indwelling object.

6. The method of claim 1, further comprising a sixth step of inserting a second guide wire through the endoscopic device brought in the first hollow organ so as to insert the second guide wire into the first hollow organ.

7. The method of claim 1, wherein in the fourth step the distal end portion of the endoscopic device grasps the part of the distal-side portion of the guide wire indwelt in the lumen of the second hollow organ, the part of the distal-side portion of the guide wire being located between a tip of the distal-side portion and the opening.

8. The method of claim 1, wherein:
the second step includes forming a part of the distal-side portion into a loop in the lumen; and
the fourth step includes causing a distal end portion of the endoscopic device to grasp the part of the distal-side, portion of the guide wire indwelt in the lumen, the part of the distal-side portion of the guide wire being located between the loop and the opening.

9. The method of claim 1, wherein in the fifth step the indwelling object is loaded on the endoscopic device inserted in the first hollow organ, and the indwelling object is indwelt in the first hollow organ.

10. The method of claim 1, further comprising a sixth step of releasing the endoscopic device from the guide wire and pulling out the endoscopic device outside of the body of the subject.

11. A method for inserting an endoscopic device into a hollow organ, the method comprising:
a first step of inserting a guide wire into a subject from outside of a body of the subject and inserting a distal end portion of the guide wire into a first hollow organ of the subject;

a second step of projecting, into a lumen of a second hollow organ, from an opening, the guide wire that is inserted into the first hollow organ, and indwelling a distal-side portion of the guide wire in the lumen, the second hollow organ communicating with the first hollow organ via the opening;

a third step of inserting an endoscopic device through a channel of a flexible endoscope that is inserted into the second hollow organ, and pushing the endoscopic device into the second hollow organ;

a fourth step of engaging a distal end portion of the endoscopic device with a part of the distal-side portion of the guide wise that is projected into the second hollow organ; and a fifth step of pulling the guide wire from the body such that the wire is pulled outside of the body by holding a portion of the guide wire that is outside of the body of the subject, thereby bringing the distal end portion of the endoscopic device in the first hollow organ from the second hollow organ via the opening, wherein the first hollow organ is either a bile duct or a pancreatic duct, the second hollow organ is a small intestine, and the opening is an anastomotic site connecting either the bile duct or the pancreatic duct to the small intestine.

12. The method of claim 11, wherein:
in the third step the endoscopic device is pushed into the second hollow organ through the channel of the flexible endoscope in a state where the endoscopic device has been loaded on the distal end portion of the endoscopic device; and
in the fifth step the guide wire is pulled from the body such that the wire is pulled outside of the body of the subject so as to bring the distal end portion of the endoscopic device in the first hollow organ from the second hollow organ via the opening together with the indwelling object.

13. The method of claim 11, further comprising a sixth step of inserting a second guide wire through the endoscopic device brought in the first hollow organ so as to insert the second guide wire into the first hollow organ.

14. The method of claim 11, wherein in the fourth step the distal end portion of the endoscopic device grasps the part of the distal-side portion of the guide wire indwelt in the lumen of the second hollow organ, the part of the distal-side portion of the guide wire being located between a tip of the distal-side portion and the opening.

15. The method of claim 11, wherein in the fifth step the indwelling object is loaded on the endoscopic device inserted in the first hollow organ, and the indwelling object is indwelt in the first hollow organ.

16. A method for inserting an endoscopic device into a hollow organ, the method comprising:
   a first step of inserting a guide wire into a subject from outside of a body of the subject and inserting a distal end portion of the guide wire into a first hollow organ of the subject;
   a second step of projecting, into a lumen of a second hollow organ, from an opening, the guide wire that is inserted into the first hollow organ, and indwelling a distal-side portion of the guide wire in the lumen, the second hollow organ communicating with the first hollow organ via the opening;
   a third step of inserting an endoscopic device through a channel of a flexible endoscope that is inserted into the second hollow organ, and pushing the endoscopic device into the second hollow organ;
   a fourth step of engaging a distal end portion of the endoscopic device with a part of the distal-side portion of the guide wire that is projected into the second hollow organ, and causing a tip of the distal end portion of the endoscopic device to grasp the part of the guide wire in a state where both the guide wire and the endoscopic device have lengthwise directions whose angles are less than 90 degrees and the guide wire extends from the distal end portion of the endoscopic ddevice; and
   a fifth step of pulling the guide wire from the body such that the wire is pulled outside of the body by holding a portion of the guide wire that is outside of the body of the subject, thereby bringing the distal end portion of the endoscopic device in the first hollow organ from the second hollow organ via the opening.

17. The method of claim 16, wherein:
   in the third step the endoscopic device is pushed into the second hollow organ through the channel of the flexible endoscope in a state where the endoscopic device has been loaded on the distal end portion of the endoscopic device; and
   in the fifth step the guide wire is pulled from the body such that the wire is pulled outside of the body of the subject so as to bring the distal end portion of the endoscopic device in the first hollow organ from the second hollow organ via the opening together with the indwelling object.

18. The method of claim 16, further comprising a sixth step of inserting a second guide wire through the endoscopic device brought in the first hollow organ so as to insert the second guide wire into the first hollow organ.

19. The method of claim 16, wherein in the fourth step the distal end portion of the endoscopic device grasps the part of the distal-side portion of the guide wire indwelt in the lumen of the second hollow organ, the part of the distal-side portion of the guide wire being located between a tip of the distal-side portion and the opening.

20. The method of claim 16, wherein in the fifth step the indwelling object is loaded on the endoscopic device inserted in the first hollow organ, and the indwelling object is indwelt in the first hollow organ.

* * * * *